(12) United States Patent
Kawanabe et al.

(10) Patent No.: US 10,405,822 B2
(45) Date of Patent: Sep. 10, 2019

(54) X-RAY CT APPARATUS

(71) Applicant: Toshiba Medical Systems Corporation, Otawara-shi (JP)

(72) Inventors: Shinya Kawanabe, Otawara (JP);
Masao Yamahana, Nasushiobara (JP);
Yasunobu Yamada, Nasushiobara (JP);
Naoki Yamashita, Nasushiobara (JP);
Ryosuke Higashi, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 247 days.

(21) Appl. No.: 15/636,115

(22) Filed: Jun. 28, 2017

(65) Prior Publication Data
US 2018/0000439 A1   Jan. 4, 2018

(30) Foreign Application Priority Data

Jun. 30, 2016 (JP) .................................. 2016-130291
Jun. 27, 2017 (JP) .................................. 2017-125460

(51) Int. Cl.
| *A61B 6/00* | (2006.01) |
| *A61B 6/03* | (2006.01) |
| *A61B 6/04* | (2006.01) |
| *G06T 11/00* | (2006.01) |
| *G06T 7/73* | (2017.01) |

(52) U.S. Cl.
CPC ............ *A61B 6/5205* (2013.01); *A61B 6/032* (2013.01); *A61B 6/0407* (2013.01); *A61B 6/542* (2013.01); *G06T 7/74* (2017.01); *G06T 11/005* (2013.01); *G06T 2207/10081* (2013.01)

(58) Field of Classification Search
CPC .... A61B 6/00; A61B 6/03; A61B 6/04; G06T 11/00; G06T 7/73; G01N 23/00
See application file for complete search history.

(56) References Cited

U.S. PATENT DOCUMENTS

2006/0140339 A1   6/2006 Marcovitch
2015/0297157 A1* 10/2015 Mukumoto .......... A61B 6/5205
                                                                 378/15

FOREIGN PATENT DOCUMENTS

| JP | 2006-513758 | 4/2006 |
| JP | 2011-24894 | 2/2011 |
| JP | 2015-213749 | 12/2015 |

* cited by examiner

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

An X-ray CT apparatus according to an embodiment includes a processing circuitry configured to acquire scan region and a first scan range, and change, while the scan region is being scanned, the first scan range to a second scan range based on projection data of the scan region acquired by the scan.

18 Claims, 8 Drawing Sheets

X-RAY CT APPARATUS

CROSS-REFERENCE TO RELATED APPLICATIONS

This application is based upon and claims the benefit of priority from Japanese Patent Application No. 2016-130291, filed on Jun. 30, 2016, and Japanese Patent Application No. 2017-125460, filed on Jun. 27, 2017; the entire contents of which are incorporated herein by reference.

FIELD

Embodiments described herein relate generally to an X-ray CT apparatus.

BACKGROUND

In conventional X-ray CT apparatuses, when a scan region the size and position of which change is scanned, a scan range is set large. In the conventional X-ray CT apparatuses, a scan ends based on an instruction input by a user who has confirmed that the entire scan region has been scanned.

However, the scan region the size and position of which change sometimes does not fit within the scan range set large. In this case, in the conventional X-ray CT apparatuses, a part of the scan region that has not fit within the scan range and a periphery thereof are additionally scanned. In the conventional X-ray CT apparatuses, three dimensional CT image data including a joint is sometimes generated since the size and position of the scan region are not necessarily same as those in the previous scan time.

In conventional X-ray CT apparatuses, even when the scan region is within the scan range set large, if a moving speed of a tabletop is fast, unnecessary range is sometimes scanned until the user inputs an instruction of making the scan ends.

DETAILED DESCRIPTION

An X-ray CT apparatus according to an embodiment includes a processing circuitry. The processing circuitry is configured to acquire a scan region and a first scan range. And the processing circuitry is configured to change, while the scan region is being scanned, the first scan range to a second scan range based on projection data of the scan region acquired by the scan.

The X-ray CT apparatus according to an embodiment is described with reference to the accompanying drawings. In the following embodiment, overlapping description will be omitted as appropriate.

Figure 1:
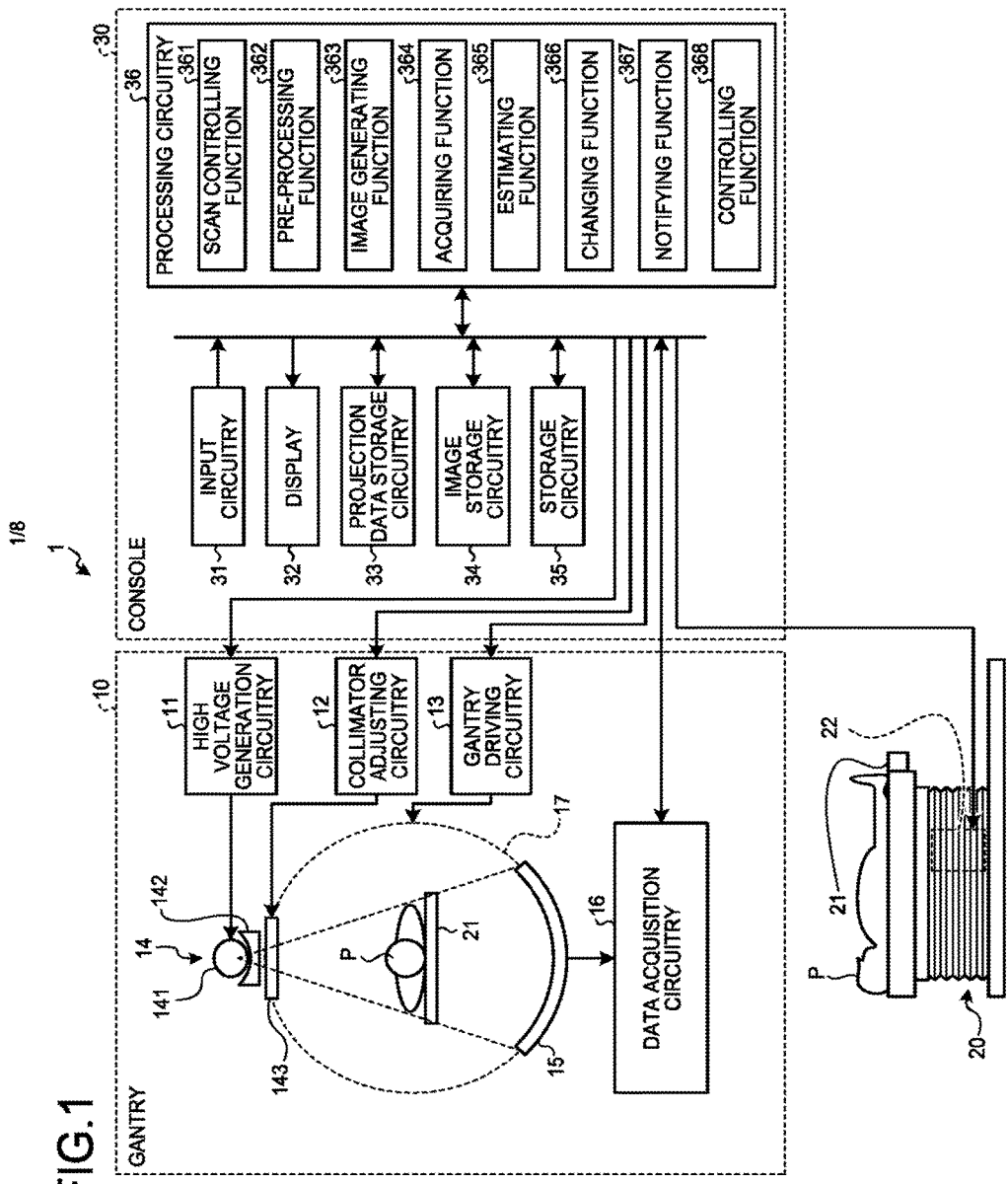
FIG. 1 is a diagram illustrating an example of a configuration of an X-ray CT apparatus according to an embodiment.

A configuration of an X-ray CT apparatus 1 according to an embodiment is described with reference to FIG. 1. FIG. 1 is a diagram illustrating an example of the configuration of the X-ray CT apparatus 1 according to the embodiment. As illustrated in FIG. 1, the X-ray CT apparatus 1 includes a gantry 10, a couch 20, and a console 30. The configuration of the X-ray CT apparatus 1 is not limited to the configuration described below.

The gantry 10 includes high voltage generation circuitry 11, collimator adjusting circuitry 12, gantry driving circuitry 13, an X-ray irradiation device 14, a detector 15, data acquisition circuitry 16, and a rotating frame 17.

The high voltage generation circuitry 11 supplies a tube voltage to an X-ray tube 141 described later. The collimator adjusting circuitry 12 adjusts the opening degree and position of a collimator 143 described later. Thereby, the collimator adjusting circuitry 12 adjusts an irradiation range in which the X-ray tube 141 irradiates a subject P with an X-ray. The gantry driving circuitry 13 rotates the rotating frame 17. Thereby, the gantry driving circuitry 13 revolves the X-ray irradiation device 14 and the detector 15 on a circular orbit centered on the subject P. The high voltage generation circuitry 11, the collimator adjusting circuitry 12, and the gantry driving circuitry 13 implement the functions by reading out computer programs stored in storage circuitry 35 described later and executing the computer programs. The high voltage generation circuitry 11, the collimator adjusting circuitry 12, and the gantry driving circuitry 13 are implemented by, for example, a processor.

The X-ray irradiation device 14 includes the X-ray tube 141, a wedge 142, and the collimator 143. The X-ray tube 141 irradiates the subject P with the X-ray. The X-ray tube 141 generates X-ray beam by the tube voltage supplied by the high voltage generation circuitry 11. The X-ray beam is also called cone beam. The wedge 142 is an X-ray filter for adjusting the X-ray dose irradiated by the X-ray tube 141. The collimator 143 is a slit for adjusting the irradiation range of the X-ray. The opening degree and position of the collimator 143 is adjusted by the collimator adjusting circuitry 12. By adjusting the opening degree of the collimator 143, for example, a fan angle and a cone angle of the cone beam are adjusted.

The detector 15 has detecting elements. These detecting elements are arranged regularly in a first direction and a second direction crossing with the first direction. For example, the first direction is a circumferential direction of the rotating frame 17, and the second direction is a slice direction. The slice direction is a body axis direction. The detecting elements detect incident X-ray intensity. Such detector is called a multi-detector row.

The detecting elements have a scintillator, a photodiode, and detection circuitry. An input terminal of the detection circuitry is connected to an output terminal of the photodiode. The output terminal of the detection circuitry is connected to the input terminal of the data acquisition circuitry 16.

The detecting elements detect incident X-ray intensity by a method as follows. First, the detecting elements convert an incident X-ray to light by the scintillator. Next, the detecting elements convert the light to an electric charge by the photodiode. Then, the detecting elements convert the electric charge to an electric signal by the detection circuitry, and output the electric signal to the data acquisition circuitry 16 described later. The detector including the detecting elements having the scintillator and the photodiode is also called a solid-state detector.

The data acquisition circuitry 16 generates projection data based on the electric signal output by the detecting elements. The projection data is, for example, a sinogram. The sinogram is data in which the signals detected by the detector 15 are arranged in each of positions of the X-ray tube 141. The positions of the X-ray tube 141 are called views. A row in the circumferential direction of the rotating frame 17 of the detecting elements in a view is called a channel. The sinogram is the data in which the X-ray intensity detected by the detector 15 is assigned to a two-dimensional rectangular coordinate system in which the first direction is defined as a view direction and the second direction crossing with the first direction is defined as a channel direction of the detector 15. The data acquisition circuitry 16 generates the sinogram row-by-row in the slice direction. The data acquisition circuitry 16 is, for example, implemented by the processor. The data acquisition circuitry 16 is also called a data acquisition system (DAS).

The rotating frame 17 is an annular frame. The rotating frame 17 holds the X-ray irradiation device 14 and the detector 15 so as to oppose each other while the subject P is interposed therebetween. The rotating frame 17 is driven by the gantry driving circuitry 13 to rotate at a high speed on a circular orbit centered on the subject P.

The couch 20 includes a tabletop 21 and couch driving circuitry 22. The tabletop 21 is a plate-like member on which the subject P is placed. The couch driving circuitry 22 moves the tabletop 21 on which the subject P is placed to the body axis direction, to move the subject P in an imaging port of the gantry 10. The couch driving circuitry 22 reads out the computer programs stored in the storage circuitry 35 described later and executes the computer program to implement the functions. The couch driving circuitry 22 is, for example, implemented by the processor.

The console 30 includes input circuitry 31, a display 32, projection data storage circuitry 33, image storage circuitry 34, the storage circuitry 35, and processing circuitry 36.

The input circuitry 31 is used by a user who inputs instructions and settings. The input circuitry 31 is, for example, included in a mouse and a keyboard. The input circuitry 31 transfers the instructions and settings input by the user to the processing circuitry 36. The input circuitry 31 is, for example, implemented by the processor.

The display 32 is a monitor referred to by the user. The display 32 is, for example, a liquid crystal display. The display 32, for example, receives an instruction to display a CT image data and a graphical user interface (GUI) from the processing circuitry 36. Thereby, the display 32 displays the CT image data and the GUI. The GUI is used when the user inputs the instructions and settings. The CT image data refers to a CT image itself, or data that is basis for displaying a CT image.

The projection data storage circuitry 33 stores the projection data applied with pre-processing by a pre-processing function 362 described later. The projection data applied with the pre-processing by the pre-processing function 362 is also called raw data. The image storage circuitry 34 stores preliminary image data generated by an image generating function 363 described later, partial image data, and CT image data.

The storage circuitry 35 stores computer programs for implementing the functions described above by the high voltage generation circuitry 11, the collimator adjusting circuitry 12, the gantry driving circuitry 13, and the data acquisition circuitry 16. The storage circuitry 35 stores the computer programs for implementing the functions described above by the couch driving circuitry 22. The storage circuitry 35 stores the computer programs for implementing each of functions described later by the processing circuitry 36.

The projection data storage circuitry 33, the image storage circuitry 34, and the storage circuitry 35 have storage media that can read out stored information by a computer. The storage media are, for example, hard disks.

The processing circuitry 36 has a scan controlling function 361, the pre-processing function 362, the image generating function 363, an acquiring function 364, an estimating function 365, a changing function 366, a notifying function 367, and a controlling function 368. The controlling function 368 is a function of operating each of the components of the gantry 10, the couch 20, and the console 30 in an appropriate timing depending on a purpose to perform a scan. Details of other functions are described later. The processing circuitry 36 is, for example, implemented by the processor.

Figure 2:
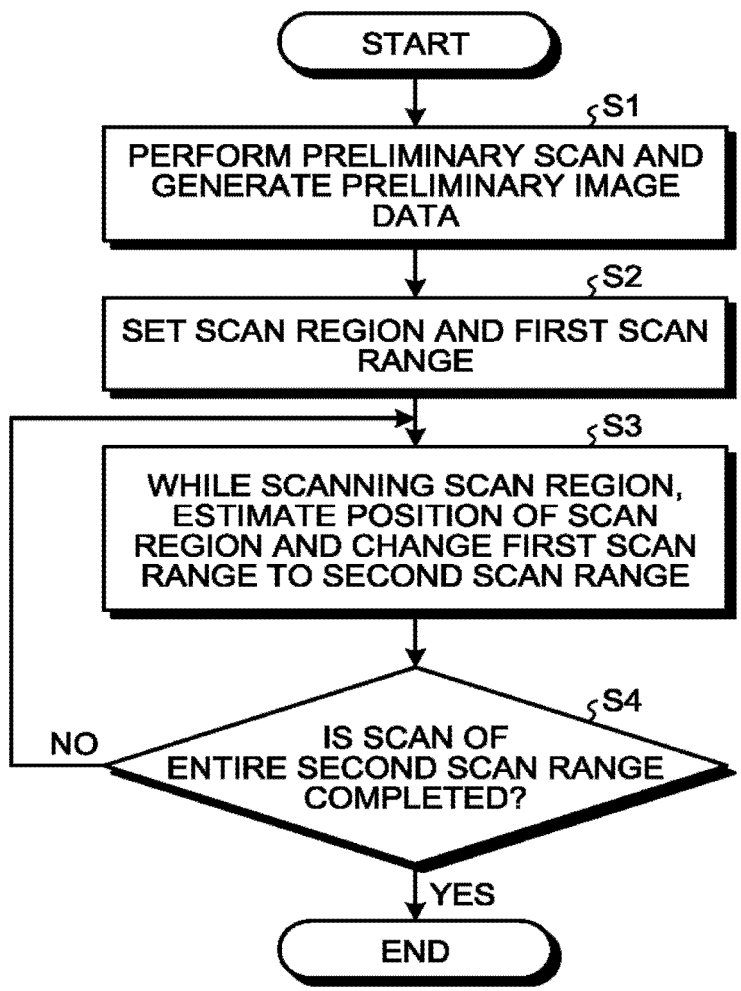
FIG. 2 is a flowchart illustrating an example of processing performed by the X-ray CT apparatus according to the embodiment.
Figure 3:
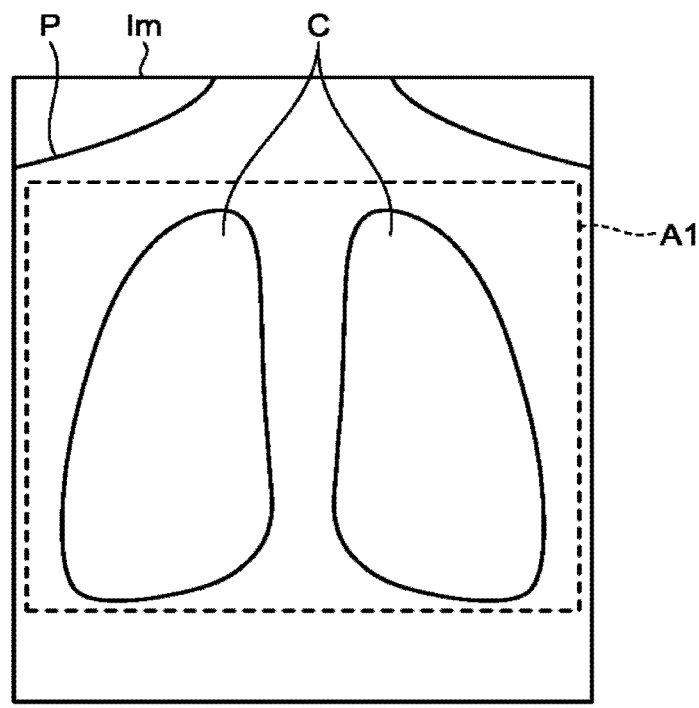
FIG. 3 is a diagram illustrating an example of a positional relation between a lung drawn in preliminary image data of the coronal plane of a subject and a first scan range.
Figure 4:
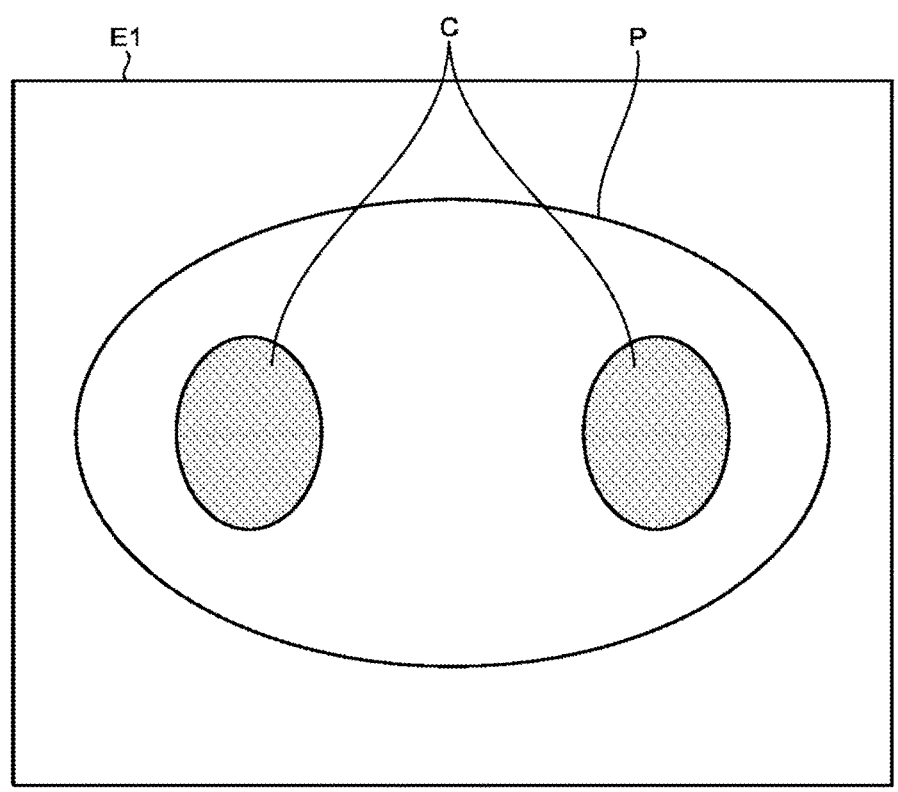
FIG. 4 is a diagram illustrating an example of partial image data of a transverse section of the subject in a terminal end of the first scan range.
Figure 5:
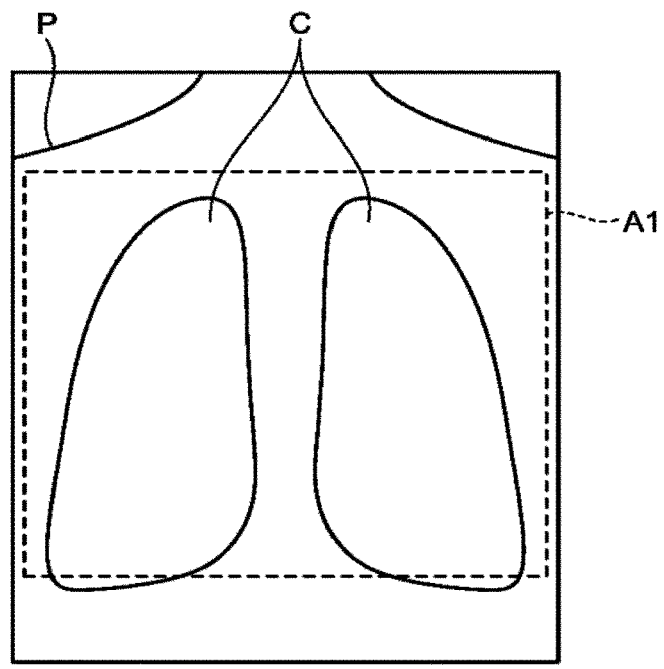
FIG. 5 is a diagram illustrating an example of a positional relation between a position of the lung estimated by the X-ray CT apparatus according to the embodiment and the first scan range.
Figure 6:
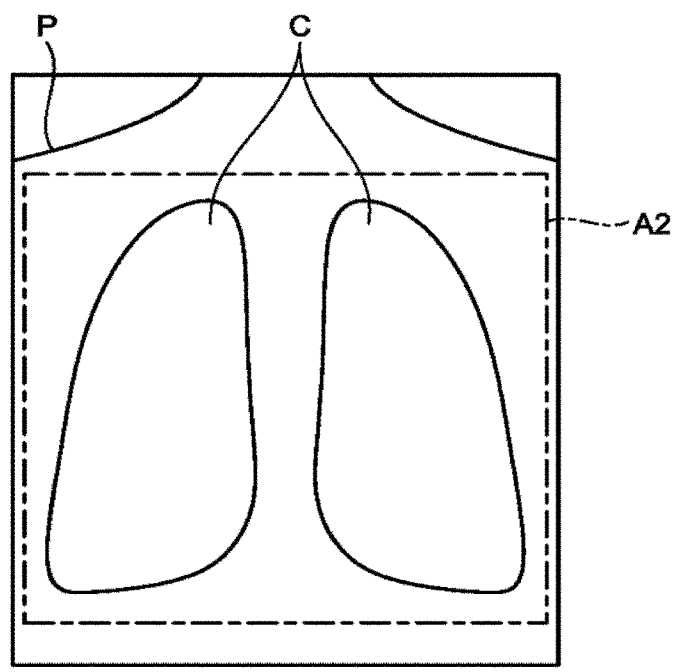
FIG. 6 is a diagram illustrating an example of a positional relation between the position of the lung estimated by the X-ray CT apparatus according to the embodiment and a second scan range.
Figure 7:
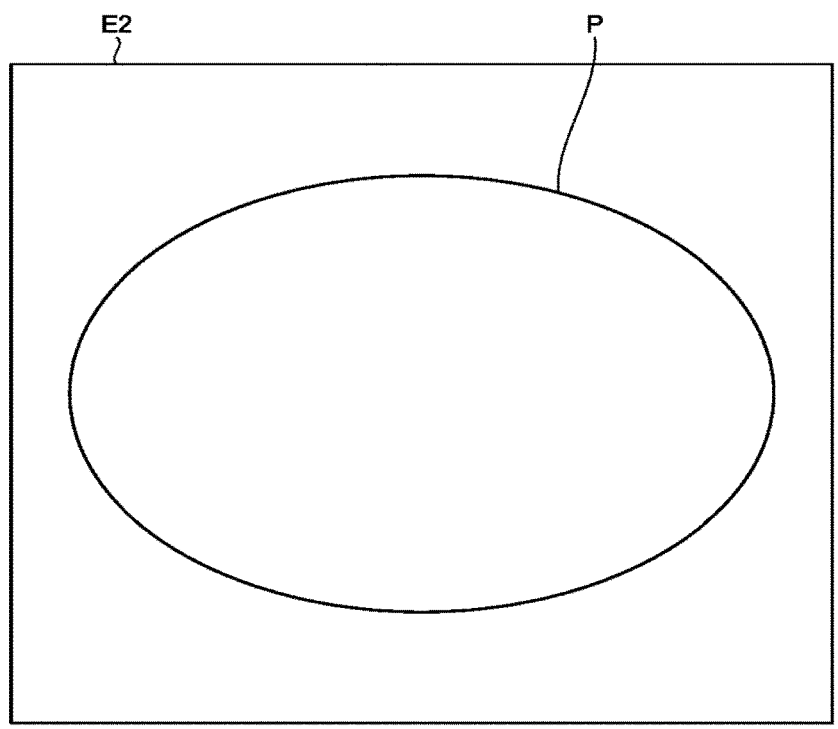
FIG. 7 is a diagram illustrating an example of partial image data of the transverse section of the subject in a terminal end of the second scan range.

An example of processing of the X-ray CT apparatus 1 according to the embodiment will be described with reference to FIG. 2 to FIG. 7. FIG. 2 is a flowchart illustrating an example of the processing performed by the X-ray CT apparatus 1 according to the embodiment. FIG. 3 is a diagram illustrating an example of a positional relation between a lung drawn in preliminary image data of the coronal plane of the subject P and a first scan range. FIG. 4 is a diagram illustrating an example of partial image data of a transverse section of the subject P in a terminal end of the first scan range. FIG. 5 is a diagram illustrating an example of a positional relation between a position of the lung estimated by the X-ray CT apparatus according to the embodiment and the first scan range. FIG. 6 is a diagram illustrating an example of a positional relation between the position of the lung estimated by the X-ray CT apparatus according to the embodiment and a second scan range. FIG. 7 is a diagram illustrating an example of partial image data of a transverse section of the subject P in a terminal end of the second scan range.

The following will describe a case where the X-ray CT apparatus 1 performs a scan of a lung C of the subject P from a head part side to an abdomen part side of the subject P, as an example. A region set to be scanned such as the "lung C" is also described as a scan region. The scan region may be set as one or a plurality of regions such as "a lung" or "a lung and a liver", and may be set as an inclusive unit such as "a chest part".

As illustrated in FIG. 2, the processing circuitry 36 performs a preliminary scan and generates preliminary image data (step S1). The processing of the step S1 is, for example, as follows.

The processing circuitry 36 reads out a computer program corresponding to the scan controlling function 361 from the storage circuitry 35 and executes the computer program. The scan controlling function 361 is a function of operating each of the components of the gantry 10, the couch 20, and the console 30 in an appropriate timing depending on a purpose to perform a scan. The processing circuitry 36 performs the scan controlling function 361 to scan the lung C of the subject P who holds his/her breath and acquire the preliminary projection data of the scan region and the periphery of the scan region.

The processing circuitry 36 may perform the preliminary scan two dimensionally or three dimensionally. For example, when the two-dimensional preliminary scan is performed, the processing circuitry 36 moves the tabletop 21 while irradiating the X-ray by the X-ray tube 141 in such a manner that the rotating frame 17 is fixed, and scans the subject P along the body axis direction. Then, the processing circuitry 36 reads out a computer program corresponding to the image generating function 363 from the storage circuitry 35 and executes the computer program to perform image generating processing to the preliminary projection data and generate the preliminary image data.

For example, when the three-dimensional preliminary scan is performed, the processing circuitry 36 moves the tabletop 21 while irradiating the X-ray by the X-ray tube 141 in such a manner that the rotating frame 17 is rotated, and helically scans the subject P along the body axis direction. Particularly, when the three-dimensional preliminary scan is performed, the processing circuitry 36 operates each of the components of the gantry 10, the couch 20, and the console 30 as follows.

The processing circuitry 36 controls the couch driving circuitry 22 to move the tabletop 21 on which the subject P is placed to the gantry 10. At the same time, the processing circuitry 36 controls the high voltage generation circuitry 11 to supply the tube voltage to the X-ray tube 141, and controls the gantry driving circuitry 13 to rotate the rotating frame 17. The processing circuitry 36 controls the collimator adjusting circuitry 12 to adjust the opening degree and the position of the collimator 143. The processing circuitry 36 controls the data acquisition circuitry 16 to acquire the preliminary projection data of the scan region and the periphery of the scan region. The X-ray dose irradiated by the X-ray tube 141 is smaller than that in a main scan described later.

The processing circuitry 36 reads out a computer program corresponding to the pre-processing function 362 from the storage circuitry 35 and executes the computer program. The pre-processing function 362 is a function of correcting the projection data generated by the data acquisition circuitry 16. This correction is, for example, a logarithmic conversion, an offset correction, a sensitivity correction, a beam hardening correction, and a scatter correction. The processing circuitry 36 performs these correction to the preliminary projection data by the pre-processing function 362.

The processing circuitry 36 reads out a computer program corresponding to the image generating function 363 from the storage circuitry 35 and executes the computer program. The image generating function 363 includes a function of reconstructing the preliminary projection data and generating the preliminary image data. The processing circuitry 36 performs the image generating function 363 to generate the preliminary image data of the scan region and the periphery of the scan region. Examples of reconstructing methods include a back projection method, and a successive approximation method. Examples of the back projection process include a filtered pack projection (FBP) method.

As illustrated in FIG. 2, the processing circuitry 36 sets the scan region and the first scan range (step S2). The processing of the step S2 is, for example, as follows.

The processing circuitry 36 reads out a computer program corresponding to the acquiring function 364 from the storage circuitry 35 and executes the computer program. The acquiring function 364 is a function of acquiring the scan region and the first scan range. For example, the processing circuitry 36 performs the acquiring function 364 to set the scan region and the first scan range.

For example, the processing circuitry 36 receives an input operation of the scan region from the user via the input circuitry 31 to set the scan region. For example, the processing circuitry 36 accesses a server that manages hospital information systems (HIS), and radiology information systems (RIS) via a network and refers to reservation information of inspection to set the scan region. As an example, the processing circuitry 36 sets the lung C of the subject P as the scan region.

In addition, for example, the processing circuitry 36 sets the first scan range based on the preliminary projection data acquired by the preliminary scan. As an example, first, the processing circuitry 36 generates the preliminary image data from the preliminary projection data acquired by the two-dimensional or three-dimensional preliminary scan. Next, the processing circuitry 36 performs processing for displaying to the generated preliminary image data to generate the preliminary image. Next, the processing circuitry 36 causes the display 32 to display the preliminary image and receives an input operation of the first scan range from the user who has referred to the preliminary image. As illustrated in FIG. 3, for example, the user inputs a region A1 including the lung C in a preliminary image Im as the first scan range. Then, the processing circuitry 36 sets the region A1 based on the input operation of the user as the first scan range.

The first scan range can be set by the processing circuitry 36, not only by user inputting. For example, the processing circuitry 36 sets the range corresponding to the scan region in the preliminary image data as the first scan range. As an example, the processing circuitry 36 sets the first scan range based on anatomical features of the scan region extracted from the preliminary image data, or a contour of the scan region drawn in the preliminary image data. Otherwise, the processing circuitry 36 sets the first scan range based on the intensity of at least a part of pixels in the preliminary projection data.

Although a case where the processing circuitry 36 sets the scan region and the first scan range has been described, the embodiment is not limited to this case. For example, the embodiment may be a case where the processing circuitry 36 acquires at least one of the scan region and the first scan range from an external device. The external device is, for example, a work station connected to the X-ray CT apparatus 1 via a network.

As an example, first, the processing circuitry 36 receives an input operation of the scan region from the user via the input circuitry 31 to set the scan region. Next, the processing circuitry 36 transmits the scan region and the preliminary image data to the external device via the network. Next, the external device sets a range corresponding to the scan region in the preliminary image data as the first scan range. Then, the processing circuitry 36 acquires the first scan range from the external device.

As another example, first, the external device receives an input operation of the scan region from the user to set the scan region. Further, the external device acquires the preliminary image data from the processing circuitry 36 via the network. Next, the external device sets a range corresponding to the scan region in the preliminary image data as the first scan range. Then, the processing circuitry 36 acquires the scan region and the first scan range from the external device.

As illustrated in FIG. 2, the processing circuitry 36 estimates, while scanning the scan region, a position of the scan region, to change the first scan range to the second scan range (step S3). The processing of the step S3 is, for example, as follows.

The processing circuitry 36 reads out a computer program corresponding to the scan controlling function 361 from the storage circuitry 35 and executes the computer program. The processing circuitry 36 helically scans the lung C of the subject P who holds his/her breath to acquire the projection data of the first scan range. The helical scan performed in the step S3 is also called a main scan.

The processing circuitry 36 reads out a computer program corresponding to the pre-processing function 362 from the storage circuitry 35 and executes the computer program. The processing circuitry 36 performs correction to the projection data by the pre-processing function 362.

The processing circuitry 36 reads out a computer program corresponding to the image generating function 363 from the storage circuitry 35 and executes the computer program. The image generating function 363 includes a function of reconstructing the projection data of the scan region acquired by the scan to generate the partial image data, while the scan region is being scanned. The processing circuitry 36 performs the image generating function 363 to reconstruct the projection data one by one, acquired by the scan performed in the step S3, and generate the partial image data. The partial image data may be data of a reconstructed slice, and may be volume data based on a plurality of slices. A reconstructing method is, for example, a back projection method, or a successive approximation method. However, it is preferable that the reconstructing method used in the step S3 be a method by which the partial image data can be generated rapidly.

The processing circuitry 36 reads out a computer program corresponding to the estimating function 365 from the storage circuitry 35 and executes the computer program. The estimating function 365 is a function of estimating the position of the scan region based on the projection data of the scan region acquired by the scan while the scan region is being scanned. For example, the processing circuitry 36 performs the estimating function 365 to estimate the position of the scan region based on the partial image data. Particularly, the processing circuitry 36 collates the partial image data with the preliminary image data to estimate the position of the scan region while the scan region is being scanned.

More particularly, the processing circuitry 36 collates the anatomical features extracted from the partial image data with the anatomical features extracted from the preliminary image data to estimate the position of the terminal end in a scan direction of the scan region. The anatomical features extracted from the partial image data are three-dimensionally distributed in the three-dimensional partial image data, and are two-dimensionally distributed in the two-dimensional partial image data. The anatomical features extracted from the preliminary image data are three-dimensionally distributed in the three-dimensional preliminary image data, and are two-dimensionally distributed in the two-dimensional preliminary image data. This estimation result is updated, as the projection data acquired by the scan performed in the step S3 is reconstructed one by one, and thereby the partial image data is updated.

Otherwise, the processing circuitry 36 estimates the position of the terminal end based on the contour of the lung C, since the shape of the contour of the lung C hardly depends on the expiratory volume of the subject P. For example, the processing circuitry 36 collates the contour of the scan region extracted from the partial image data with the contour of the scan region extracted from the preliminary image data to estimate the position of the terminal end in the scan direction of the scan region. For example, the processing circuitry 36 collates these two contours by making the contour of an upper part of the lung C extracted from the partial image data same as the contour of the upper part of the lung C extracted from the preliminary image data, to estimate the position of the terminal end in the scan direction of the lung C since the contour and volume of the upper part of the lung C hardly depend on the expiratory volume of the subject P. This estimation result is updated, as the projection data acquired by the scan performed in the step S3 is reconstructed one by one, and thereby the partial image data is updated. The contours described here include a two-dimensional contour and a three-dimensional contour.

Otherwise, the processing circuitry 36 estimates the position of the terminal end in the scan direction of the scan region based on the ratio between an area of the scan region extracted from the partial image data and an area of the scan region extracted from the preliminary image data. This estimation result is updated, as the projection data acquired by the scan performed in the step S3 is reconstructed one by one, and thereby the partial image data is updated.

Further, together with the estimation of the position of the scan region described above, when the scan region is drawn in the partial image data in the terminal end of the first scan range, the processing circuitry 36 estimates that the terminal end in the scan direction of the scan region is outside of the first scan range. For example, when the lung C that is the scan region is drawn in partial image data E1 in the terminal end of the first scan range as illustrated in FIG. 4, the processing circuitry 36 estimates that the terminal end in the body axis direction of the lung C is outside of the first scan range (region A1) as illustrated in FIG. 5. When the expiratory volume of the subject P in the step S3 is larger than the expiratory volume of the subject P in the step S1, the volume of the lung C in the step S3 is larger than the volume of the lung C in the step S1. Thus, the terminal end in the body axis direction of the lung C is sometimes located outside of the first scan range.

In this case, the processing circuitry 36 may compare the preliminary image data in the terminal end of the first scan range with the partial image data in the terminal end of the first scan range, and estimate that the terminal end in the scan direction of the scan region is outside of the first scan range. That is, when the lung C is not drawn in the preliminary image data in the terminal end of the first scan range, and the lung C is drawn in the partial image data in the terminal end of the first scan range, the processing circuitry 36 can estimate that the terminal end in the scan direction of the scan region is outside of the first scan range by comparing both data.

The processing circuitry 36 reads out a computer program corresponding to the changing function 366 from the storage circuitry 35 and executes the computer program. The processing circuitry 36 changes the first scan range to the second scan range based on the estimated position of the scan region. For example, the processing circuitry 36 estimates the volume of the second scan range, that is, the position of the terminal end of the second scan range based on the result of collating the anatomical features extracted from the partial image data with the anatomical features extracted from the preliminary image data, and the result of collating the contour of the scan region extracted from the partial image data with the contour of the scan region extracted from the preliminary image data. Next, the processing circuitry 36 determines the volume of the second scan range, that is, the position of the terminal end of the second scan range based on the scan region drawn in the partial image data in the terminal end of the first scan range. The processing circuitry 36 changes the first scan range to the second scan range including the entire scan region based on the position of the scan region estimated by the estimating function 365 while the scan region is being scanned. For example, as illustrated in FIG. 6, the processing circuitry 36 sets a region A2 as the second scan range. The region A2 includes the entire lung C that is the scan region.

The processing circuitry 36 reads out a computer program corresponding to the notifying function 367 from the storage circuitry 35 and executes the computer program. The processing circuitry 36 notifies that the first scan range has been changed to the second scan range. For example, the processing circuitry 36 performs the notifying function 367 to notify that the first scan range has been changed to the second scan range that is larger than the first scan range by the changing function 366. A method of notifying that the first scan range is changed to the second scan range is not limited particularly. The processing circuitry 36 may perform the notifying function 367 to, for example, display a message and an icon that indicate that the first scan range is changed to the second scan range on the display 32. Otherwise, the processing circuitry 36 may perform the notifying function 367 to generate a sound that notifies that the first scan range has been changed to the second scan range.

As illustrated in FIG. 2, the processing circuitry 36 performs the scan controlling function 361 to determine whether the scan of the entire second scan range has been completed (step S4). For example, when the lung C that is the scan region is not drawn in partial image data E2 in the terminal end of the second scan range as illustrated in FIG. 7, the processing circuitry 36 determines that the scan of the entire second scan range has been completed. If it is determined that the scan of the entire second scan range has been completed (step S4 Yes), the processing circuitry 36 ends the processing. For example, when the lung C that is the scan region is drawn in the partial image data in the terminal end of the second scan range, the processing circuitry 36 determines that the scan of the entire second scan range has not been completed. If it is determined that the scan of the entire second scan range has not been completed (step S4 No), the processing circuitry 36 returns the processing to the step S3. In this case, the second scan range in the step S4 is regarded as the first scan range in the step S3.

The X-ray CT apparatus 1 according to the embodiment has been described above. As described above, while the scan region is being scanned, the X-ray CT apparatus 1 estimates the position of the scan region based on the projection data of the scan region acquired by the scan and changes the first scan range to the second scan range including the entire scan region based on the estimated position of the scan region. Thus, the X-ray CT apparatus 1 can reliably scan the entire scan region by one time scan. In addition, the X-ray CT apparatus 1 can prevent the CT image data of the scan region from including a joint. Further, the X-ray CT apparatus 1 does not need to additionally scan the scan region and does not scan unnecessary range. Thus, the X-ray irradiation dose to the subject P can be reduced.

The X-ray CT apparatus 1 described above estimates the position of the terminal end of the second scan range based on the preliminary image data and the partial image data. Then, the X-ray CT apparatus 1 changes the first scan range to the second scan range including the entire scan region based on this estimation result. Thus, the X-ray CT apparatus 1 can promptly change the first scan range to the second scan range that has a volume as small as possible, and improve throughput. This processing performed by the X-ray CT apparatus 1 is especially effective when the scan of the scan region is completed in a short time.

The following describes modification of the embodiment described above.

The processing circuitry 36 may perform processing as follows instead of the processing described above, in the step S3 in FIG. 2. The processing circuitry 36 may perform the estimating function 365 to estimate the position of the terminal end in the scan direction of the scan region based on the anatomical features extracted from the partial image data. Otherwise, the processing circuitry 36 may perform the estimating function 365 to estimate the position of the terminal end in the scan direction of the scan region based on the contour of the scan region extracted from the partial image data. In these cases, the preliminary image data is used only in the setting of the first scan range performed in the step S2 in FIG. 2.

Next, the processing circuitry 36 performs the changing function 366 to estimate the volume of the second scan range, that is, the position of the terminal end of the second scan range, based on the position of the terminal end in the scan direction of the scan region estimated based on the anatomical features extracted from the partial image data, or based on the position of the terminal end in the scan direction of the scan region estimated based on the contour of the scan region extracted from the partial image data. Then, the processing circuitry 36 changes the first scan range to the second scan range including the entire scan region based on the position of the scan region estimated by the estimating function 365 while the scan region is being scanned.

The processing circuitry 36 may not perform the processing of the step S1 in FIG. 2. That is, the processing circuitry 36 may not perform the preliminary scan to generate the preliminary image data. In this case, the processing circuitry 36 sets the scan region and the first scan range by a predetermined method in the step S2 in FIG. 2. In addition, the processing circuitry 36 performs the estimating function 365 to estimate the position of the terminal end in the scan direction of the scan region based on the anatomical features extracted from the partial image data in the step S3 in FIG. 2. Otherwise, the processing circuitry 36 performs the estimating function 365 to estimate the position of the terminal end in the scan direction of the scan region based on the contour of the scan region extracted from the partial image data in the step S3 in FIG. 2.

The processing circuitry 36 may perform the estimating function 365 to estimate the position of the scan region based on the intensity of at least a part of pixels in the projection data of the scan region instead of the partial image data of the scan region, in the step S3 in FIG. 2. For example, the processing circuitry 36 estimates the position of the scan region in a transverse section of the subject P based on the meandering way of the region having the intensity corresponding to the scan region in the projection data acquired in the step S3 in FIG. 2. In addition, the processing circuitry 36 estimates the position of the scan region in the coronal plane and the sagittal plane of the subject P based on the change of the width of the channel direction in the view direction of the region having the intensity corresponding to the scan region in the projection data acquired in the step S3 in FIG. 2.

The processing circuitry 36 may perform the acquiring function 364 to set the first scan range based on the preliminary projection data, not the preliminary image data, in the step S2 in FIG. 2. For example, the processing circuitry 36 specifies the position of the scan region in the transverse section of the subject P based on the meandering way of the region having the intensity corresponding to the scan region in the preliminary projection data acquired in the step S1 in FIG. 2. In addition, the processing circuitry 36 specifies the position of the scan region in the coronal plane and the sagittal plane of the subject P based on the change of the width of the channel direction in the view direction of the region having the intensity corresponding to the scan region in the preliminary projection data acquired in the step S1 in FIG. 2. Then, the processing circuitry 36 performs the acquiring function 364 to set the first scan range including the entire scan region in the step S2 in FIG. 2.

The processing circuitry 36 may perform the estimating function 365 to collate the projection data of the scan region with the preliminary projection data, instead of collating the partial image data with the preliminary image data, and estimate the position of the scan region, while the scan region is being scanned, in the step S3 in FIG. 2. Thereby, the processing circuitry 36 does not need to perform the image generating function 363 to reconstruct the projection data. Thus, the processing circuitry 36 can promptly estimate the position of the scan region.

The processing circuitry 36 may perform the changing function 366 to change the first scan range to the second scan range that is smaller than the first scan range when the estimating function 365 has estimated that the entire scan region is in the first scan range. Even in this case, the second scan range includes the entire scan region. Otherwise, the processing circuitry 36 may perform the changing function 366 to change the first scan range to the second scan range that has equal position and volume to that of the first scan range when the estimating function 365 has estimated that the entire scan region is in the first scan range. Thus, the processing circuitry 36 can reliably scan the entire scan region by one time scan, while the X-ray irradiation dose to the subject P can be reduced.

The processing circuitry 36 may perform the scan controlling function 361 to reduce the helical pitch by reducing the moving speed of the tabletop 21 when the volume of a range that has not been scanned in the second scan range is equal to or smaller than a threshold value. Thus, the processing circuitry 36 can reliably end the scan in the terminal end of the second scan range. In addition, the processing circuitry 36 may perform the scan controlling function 361 to control a tube current of the X-ray tube 141 so that the X-ray irradiation dose to the subject P is same as that in a case where the volume of the range that has not been scanned in the second scan range is larger than the threshold value, according to the reduction of the moving speed of the tabletop 21. Thus, the processing circuitry 36 can prevent the irradiation dose to the subject P from increasing by reducing the moving speed of the tabletop 21.

The processing circuitry 36 may perform the scan controlling function 361 to adjust the opening degree and the position of the collimator 143 so that the range other than the second scan range is not irradiated with the X-ray when the volume of the range that has not been scanned in the second scan range is equal to or smaller than a threshold value. Such control by the collimator 143 is also called an active collimator. Thereby, the processing circuitry 36 can prevent the X-ray irradiation dose of the subject P from increasing unnecessarily.

In the embodiment described above, a case where the X-ray CT apparatus 1 scans the lung C that is the scan region from the head part side to the abdomen part side of the subject P is described as an example. However, the embodiment is not limited to this case. The X-ray CT apparatus 1 may scan the lung C that is the scan region from the abdomen part side to the head part side of the subject P. However, the lung C expands to the abdomen part side of the subject P when the subject P inhales. Therefore, it is preferable that, when the scan region is the lung C, the X-ray CT apparatus 1 scan the lung C from the head part side to the abdomen part side of the subject P. In addition, the embodiment described above can be applied also to a case where the scan region is repeatedly scanned. Further, the embodiment described above can be applied also to a case where the scan region is other than the lung C.

In the embodiment described above, a case where the position of the scan region is estimated, and the first scan range is changed to the second scan range based on the estimated position, has been described. However, the embodiment is not limited to this case. For example, the processing circuitry 36 can change the first scan range to the second scan range based on the slice reconstructed in real time from the acquired projection data while the scan region is being scanned.

The following describes a case where the scan region is the lung C for a case where the scan range is changed based on the slice, as an example. First, the processing circuitry 36 acquires the scan region and the first scan range and starts the scan. Here, the processing circuitry 36 reconstructs the slice based on the acquired projection data while the lung C is being scanned. In addition, the processing circuitry 36 determines in real time whether the reconstructed slice includes the lung C. For example, the processing circuitry 36 can determine whether the slice includes the lung C based on that the lung C is filled with air and the CT value of the air is extremely smaller than the body tissue. Note that the processing circuitry 36 may reduce the helical pitch after the volume of a range that has not been scanned in the first scan range is equal to or smaller than the threshold value.

When determining that the reconstructed slice does not include the lung C, the processing circuitry 36 changes the first scan range to the second scan range the terminal end of which is a position where the slice does not include the lung C anymore. That is, the processing circuitry 36 ends the scan at a time when the slice that is reconstructed in real time does not include the lung C anymore. Thereby, the processing circuitry 36 can reduce the radiation dose of the subject P and can reliably scan the lung C by one time scan.

In the embodiment described above, a case where the scan is performed up to the terminal end of the scan region has been described. However, the embodiment is not limited to this case. For example, the embodiment may be a case where the processing circuitry 36 further performs the scan for a predetermined volume from the terminal end of the scan region. The predetermined volume may be a condition set by the user before the start of the main scan or may be a fixed condition.

For example, the predetermined volume is set by using a length from the terminal end of the scan region. In this case, the subject P is three-dimensionally scanned for the set "length" from the terminal end of the scan region. That is, by setting the "length", the predetermined volume can be set. As an example, the predetermined volume is set as "3 cm from the terminal end of the lung C".

In addition, for example, the predetermined volume is set by using a region in a periphery of the scan region. When the scan region is the lung C, examples of the region in the periphery of the scan region include a liver L. As an example, the predetermined volume is set as "up to a position where a transverse sectional area of the liver is a predetermined area". In this case, the subject P is three-dimensionally scanned up to the "position" set from the terminal end of the scan region. That is, by setting the "position", the predetermined volume can be set.

Figure 8:
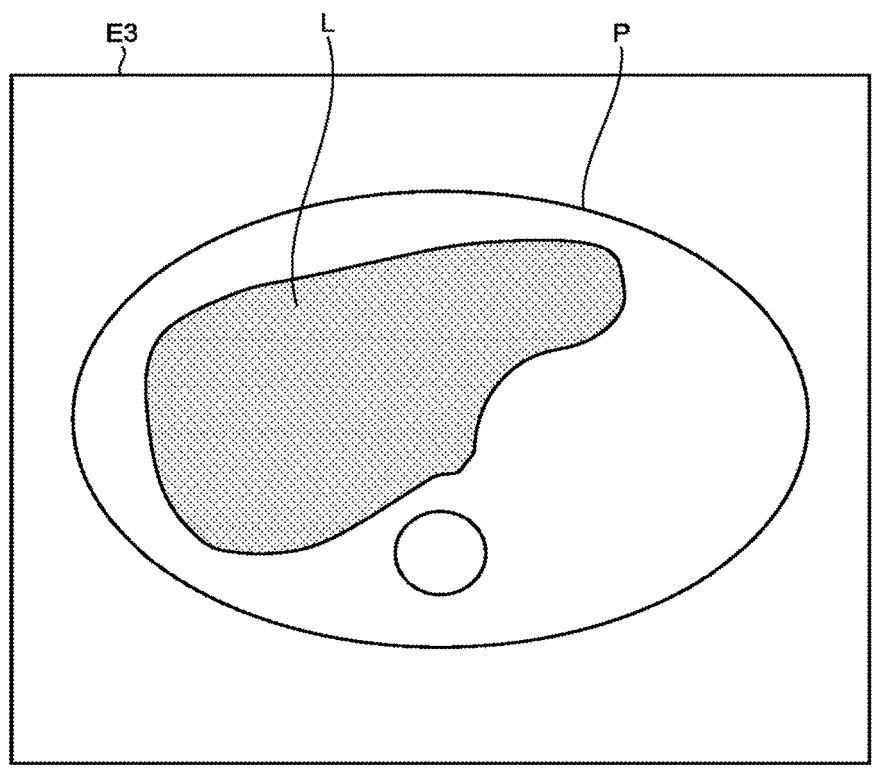
FIG. 8 is a diagram for explaining a case where a scan is further performed for a predetermined volume.
Figure 9:
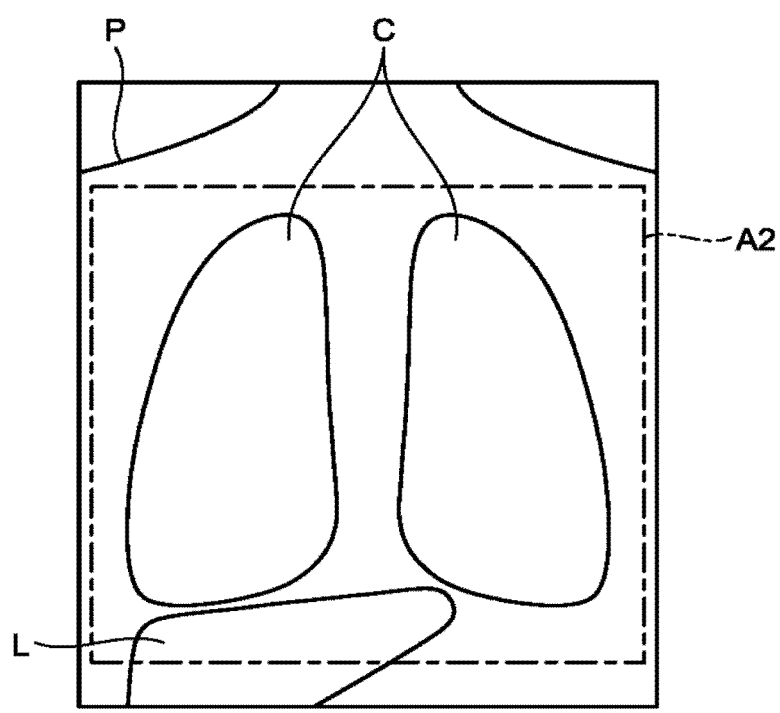
FIG. 9 is a diagram for explaining the case where the scan is further performed for the predetermined volume.

A case where the scan is further performed for the predetermined volume from the terminal end of the scan region will be described with reference to FIG. 8 and FIG. 9. FIG. 8 and FIG. 9 are diagrams for explaining the case where the scan is further performed for the predetermined volume.

First, the processing circuitry 36 acquires the first scan range. For example, the processing circuitry 36 sets a range from an upper end of the lung C to the position where the transverse sectional area of the liver L is the predetermined area, as the first scan range, in the three-dimensionally acquired preliminary image data. Next, the processing circuitry 36 starts the scan and reconstructs the slice in real time. When the slice includes the liver L, the processing circuitry 36 acquires the transverse sectional area of the liver L in the slice in real time. For example, the processing circuitry 36 acquires the area of the liver L in partial image data E3 as illustrated in FIG. 8. The processing circuitry 36 may reduce the helical pitch after the volume of a range that has not been scanned in the first scan range is equal to or smaller than a threshold value.

Then, the processing circuitry 36 changes the first scan range to the second scan range the terminal end of which is the position where the transverse sectional area of the liver L is the predetermined area. Particularly, the processing circuitry 36 sets the position of the terminal end of the second scan range as the predetermined position in the body axis direction of the liver L as illustrated in FIG. 9. That is, the processing circuitry 36 changes the first scan range to the second scan range that is increased for the predetermined volume from the position where the scan of the lung C is completed, and ends the scan at a time when the scan is performed for the predetermined volume from the terminal end of the lung C. Thereby, the processing circuitry 36 can reduce the radiation dose of the subject P and can reliably perform the scan of the lung C and the scan for the predetermined volume by one time scan.

Examples of the processors described above include a central processing unit (CPU), a graphics processing unit (GPU), an application specific integrated circuit (ASIC), a programmable logic device (PLD), and a field programmable gate array (FPGA). Examples of the programmable logic devices (PLDs) include a simple programmable logic device (SPLD), and a complex programmable logic device (CPLD).

In the embodiment described above, the high voltage generation circuitry 11, the collimator adjusting circuitry 12, the gantry driving circuitry 13, the data acquisition circuitry 16, the couch driving circuitry 22, and the processing circuitry 36 read out the computer programs stored in the storage circuitry 35 and execute the computer programs to implement the functions. However, the embodiment is not limited to this. Instead of storing the computer programs in the storage circuitry 35, the computer programs may be directly integrated in the circuitry respectively. In this case, the circuitry read out the computer programs directly integrated and execute the computer programs to implement the functions.

Each of the circuitry illustrated in FIG. 1 may be dispersed or integrated as appropriate. For example, the processing circuitry 36 may be dispersed to scan controlling circuitry, pre-processing circuitry, image generating circuitry, acquiring circuitry, estimating circuitry, changing circuitry, notifying circuitry, and controlling circuitry that perform respectively the functions of the scan controlling function 361, the pre-processing function 362, the image generating function 363, the acquiring function 364, the estimating function 365, the changing function 366, the notifying function 367, and the controlling function 368. In addition, for example, the high voltage generation circuitry 11, the collimator adjusting circuitry 12, the gantry driving circuitry 13, the data acquisition circuitry 16, the couch driving circuitry 22, and the processing circuitry 36 may be integrated optionally.

According to at least one of the embodiments described above, the scan region can be reliably scanned by one time scan.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising processing circuitry configured to
    acquire a scan region and a first scan range, and
    change, while the scan region is being scanned, the first scan range to a second scan range based on projection data of the scan region acquired by the scan.

2. The X-ray CT apparatus according to claim 1, wherein the processing circuitry is configured to
    estimate, while the scan region is being scanned, a position of the scan region based on the projection data of the scan region acquired by the scan, and
    change, while the scan region is being scanned, the first scan range to the second scan range including the entire scan region based on the estimated position of the scan region.

3. The X-ray CT apparatus according to claim 2, wherein the processing circuitry is configured to
    reconstruct, while the scan region is being scanned, the projection data related to the scan region acquired by the scan to generate partial image data, and
    estimate the position of the scan region based on the partial image data.

4. The X-ray CT apparatus according to claim 3, wherein the processing circuitry is configured to estimate that a terminal end in a scan direction of the scan region is outside of the first scan range when the scan region is drawn in the partial image data in a terminal end of the first scan range.

5. The X-ray CT apparatus according to claim 3, wherein the processing circuitry is configured to estimate the position of the terminal end in the scan direction of the scan region based on anatomical features extracted from the partial image data.

6. The X-ray CT apparatus according to claim 3, wherein the processing circuitry is configured to estimate the position of the terminal end in the scan direction of the scan region based on a contour of the scan region extracted from the partial image data.

7. The X-ray CT apparatus according to claim 3, wherein the processing circuitry is configured to
    acquire the first scan range based on preliminary projection data acquired by a preliminary scan,
    generate preliminary image data from the preliminary projection data, and
    while the scan region is being scanned, collate the partial image data with the preliminary image data to estimate the position of the scan region.

8. The X-ray CT apparatus according to claim 7, wherein the processing circuitry is configured to collate anatomical features extracted from the partial image data with anatomical features extracted from the preliminary image data to estimate the position of the terminal end in the scan direction of the scan region.

9. The X-ray CT apparatus according to claim 7, wherein the processing circuitry is configured to collate a contour of the scan region extracted from the partial image data with a contour of the scan region extracted from the preliminary image data to estimate the position of the terminal end in the scan direction of the scan region.

10. The X-ray CT apparatus according to claim 7, wherein the processing circuitry is configured to estimate the position of the terminal end in the scan direction of the scan region based on a ratio between an area of the scan region extracted from the partial image data and an area of the scan region extracted from the preliminary image data.

11. The X-ray CT apparatus according to claim 2, wherein the processing circuitry is configured to estimate the position of the scan region based on the intensity of at least a part of pixels in the projection data of the scan region.

12. The X-ray CT apparatus according to claim 2, wherein the processing circuitry is configured to
    acquire the first scan range based on preliminary projection data acquired by a preliminary scan, and
    while the scan region is being scanned, collate the projection data of the scan region with the preliminary projection data to estimate the position of the scan region.

13. The X-ray CT apparatus according to claim 1, wherein the processing circuitry is configured to change the first scan range to the second scan range that is increased for a predetermined volume from a position where the scan of the scan region is completed.

14. The X-ray CT apparatus according to claim 1, wherein the processing circuitry is configured to further notify that the first scan range has been changed to the second scan range.

15. The X-ray CT apparatus according to claim 14, wherein the processing circuitry is configured to notify that the first scan range has been changed to the second scan range larger than the first scan range.

16. The X-ray CT apparatus according to claim 2, wherein the processing circuitry is configured to change the first scan range to the second scan range smaller than the first scan range when estimating that the entire scan region is in the first scan range.

17. The X-ray CT apparatus according to claim 1, wherein the processing circuitry is configured to reduce the moving speed of a tabletop to reduce a helical pitch when the volume of a range that has not been scanned in the second scan range is equal to or smaller than a threshold value.

18. The X-ray CT apparatus according to claim 17, wherein the processing circuitry is configured to control a tube current of an X-ray tube so that an X-ray irradiation dose to a subject is same as that in a case where the volume of the range that has not been scanned in the second scan range is larger than the threshold value, according to the reduction of the moving speed of the tabletop.

* * * * *